United States Patent [19]

Boeck et al.

[11] Patent Number: 4,558,009
[45] Date of Patent: Dec. 10, 1985

[54] PROCESS FOR PRODUCING ANTIBIOTIC A-51568 BY FERMENTATION AND MICROORGANISM

[75] Inventors: LaVerne D. Boeck; Marvin M. Hoehn; Gary G. Marconi, all of Indianapolis, Ind.

[73] Assignee: Eli Lilly and Company, Indianapolis, Ind.

[21] Appl. No.: 565,314

[22] Filed: Dec. 27, 1983

Related U.S. Application Data

[63] Continuation-in-part of Ser. No. 450,880, Dec. 20, 1982, abandoned.

[51] Int. Cl.$^4$ .................... C12P 19/60; C12N 1/20; C12R 1/365
[52] U.S. Cl. ........................................ 435/75; 435/253; 435/872
[58] Field of Search .................... 435/75, 253, 872

[56] References Cited

U.S. PATENT DOCUMENTS

| | | | |
|---|---|---|---|
| 3,067,099 | 12/1962 | McCormick | 167/65 |
| 3,333,786 | 8/1967 | Kunstmann et al. | 167/65 |
| 3,952,095 | 4/1976 | Hamill et al. | 424/118 |
| 4,322,343 | 3/1982 | Debono | 260/112.5 R |
| 4,322,406 | 3/1982 | Debono et al. | 424/118 |

FOREIGN PATENT DOCUMENTS 0765886  1/1957  United Kingdom .

OTHER PUBLICATIONS

Williamsom et al., "Structure Revision of the Antibiotic Vancomycin. The Use of Nuclear Overhauser Effect Difference Spectroscopy", *J. Am. Chem. Soc.* 103, 6580–6585 (1981).

Kalman et al., "An NMR Study of the Antibiotic Ristocetin A. The Negative Nuclear Overhauser Effect in Structure Elucidation" *J. Am. Chem. Soc.* 102, 897–905 (1980).

Ellestad et al., "Avoparcin and Epiavoparcin", *J. Am. Chem. Soc.* 103, 6522–6524 (1981).

*Primary Examiner*—Lionel M. Shapiro
*Attorney, Agent, or Firm*—Paul C. Steinhardt; Arthur R. Whale

[57] ABSTRACT

Antibiotic A-51568 is produced by submerged, aerobic fermentation of new *Nocardia orientalis* NRRL 15232. The antibiotic is effective against gram-positive organisms.

2 Claims, 1 Drawing Figure

Figure 1

PROCESS FOR PRODUCING ANTIBIOTIC A-51568 BY FERMENTATION AND MICROORGANISM

CROSS REFERENCE TO RELATED APPLICATION

This is a continuation-in-part of co-pending application Ser. No. 450,880, filed Dec. 20, 1982, now abandoned.

BACKGROUND OF THE INVENTION

A great many microorganisms are pathogenic and are causative agents of disease states in both humans and animals.

Over the years, a great number of antibiotics which are active against pathogenic microorganisms have been developed. However, there is still a need to find agents which are more effective against these pathogenic microorganisms in order to more successfully treat the diseases caused by the microorganisms in humans or animals.

Antibiotic A-51568, belonging to the glycopeptide family of antibiotics, is a gram-positive antimicrobial agent.

Glycopeptide antibiotics already known in the art include, inter alia, vancomycin, McCormick et al., U.S. Pat. No. 3,067,099 (Dec. 4, 1962), the structure of vancomycin being reported by Williamson et al., *J. Am. Chem. Soc.* 103, 6580–6585 (1981); actaplanin (antibiotic A-4696), Hamill et al., U.S. Pat. No. 3,952,095 (Apr. 20, 1976), a portion of the structure of actaplanin being reported by Debono, U.S. Pat. No. 4,322,343 (Mar. 30, 1982); ristocetin, British Pat. No. 765,886 (1957), the structure of ristocetin A, one factor of the ristocetin complex, being reported by Kalman et al., *J. Am. Chem. Soc.* 102, 897–905 (1980); and avoparcin, Kunstmann et al., U.S. Pat. No. 3,338,786 (Aug. 29, 1967), the structure of avoparcin being described by Ellestad et al., *J. Am. Chem. Soc.* 103, 6522–6524 (1981).

SUMMARY OF THE INVENTION

This invention relates to demethylvancomycin designated herein as antibiotic A-51568, which is produced by culturing a hitherto undescribed microorganism, *Nocardia orientalis* NRRL 15232, or an A-51568-producing mutant or variant thereof, under submerged aerobic fermentation conditions. *Nocardia orientalis* NRRL 15232 is also referred to herein as the A-51568.1 strain.

This antibiotic inhibits the growth of pathogenic microorganisms, in particular, those within the gram-positive genera Staphylococcus and Streptococcus, which are resistant to penicillin.

Culturing the A-51568.1 strain under submerged aerobic conditions also produces a minor amount of the novel antibiotic A-51568B, which is a glycopeptide analogue differing from the instant A-51568 and which is described in U.S. application Ser. No. 561,008, filed Dec. 13, 1983 by LaVerne D. Boeck, Marvin M. Hoehn and Gary G. Marconi, herein incorporated by reference. As will be recognized by those familiar with antibiotic production by fermentation, A-51568 and A-51568B will be produced in varying ratios depending upon the fermentation conditions used. A-51568 is generally produced in a greater amount than A-51568B. Both A-51568 and A-51568B are removed from broth filtrate by adsorbtion onto Diaion HP-20 resin and are eluted with 50% water/methanol after the resin was first washed with water and 25 percent methanol in water. A-51568 and A-51568B are further purified, then separated by column chromatography and high performance liquid chromatography.

DESCRIPTION OF THE DRAWINGS

The infrared absorption spectrum of antibiotic A-51568, run in KBr pellet, is presented in the accompanying drawing, labeled FIG. 1.

DETAILED DESCRIPTION OF THE INVENTION

This invention relates to demethylvanomycin (A-51568) having the following structural formula to its preparation, and to the pharmaceutically-acceptable, non-toxic salts of the antibiotic.

Antibiotic A-51568 is a white, amorphous solid. Elemental analysis of antibiotic A-51568 indicates the following approximate percentage composition: 50.63 percent carbon, 5.07 percent hydrogen, 8.36 percent nitrogen, 8.19 percent chlorine, and 25.16 percent oxygen. The antibiotic has a molecular weight of about 1435, as determined by fast-atom-bombardment mass spectrometry.

The proton nuclear magnetic resonance spectrum of antibiotic A-51568 was determined in dimethylsulfoxide at 60° C. and 360 MHz. The several six-membered rings of the structural formula are identified by letters of the alphabet, as indicated in the following formula:

The table of Chemical Shifts, in ppm, follows in Table 1.

TABLE 1

Chemical Shifts

| Assignment | | Assignment | |
|---|---|---|---|
| Ring A | | | |
| Chem. Shift | Chem. Shift | Asparagine | |
| —NH | 6.54 | —NH | 6.61 |
| -2' | 4.19 | -α | 4.32 |
| -1' | 5.14 | -β's | 2.56 & |
| —OH | 5.86 | | 2.14 |
| -2 | 7.86 | —NH$_2$ | 7.29 & |
| -5 | 7.30 | | 6.83 |
| -6 | 7.47 | | |
| Ring B | | Leucine | |
| | | —NH$_2$ | —* |
| —NH | 8.24 | -α | 3.70 |
| -1' | 5.72 | -β's | 1.65 & |
| -2 | 5.68 | | 1.49 |
| -6 | 5.22 | -γ | 1.76 |
| | | -δ's | 0.93 & |
| | | | 0.90 |
| Ring C | | Glucose | |
| —NH | —* | -1 | 5.33 |
| -2' | 4.78 | -2 | 3.58 |
| -1' | 5.18 | -3 | 3.49 |
| —OH | 5.74 | -4 | 3.29 |
| -2 | 7.66 | -5 | * |
| -3 | 7.18 | -6 | 3.70 & |
| -6 | 7.42 | | 3.54 |
| Ring D | Chem. Shift | Vancosamine | Chem. Shift |
| —NH | 8.45 | -1 | 5.30 |
| -1' | 4.47 | -2 | 1.93 & |
| -2 | 6.26 | | 1.77 |
| -4 | 6.42 | (3-CH$_3$) | 1.37 |
| Ring E | | | |
| | | 4 | * |
| —NH | 8.54 | 5 | 4.67 |
| -1' | 4.47 | (5-CH$_3$) | 1.09 |
| -2 | 7.17 | | |
| -5 | 6.72 | | |
| -6 | 6.79 | | |

*Not assigned

The proton nuclear magnetic resonance spectrum of antibiotic A-51568 is very much like that of Vancomycin B. The chief difference noticeable by inspection is the absence in the spectrum of A-51568 (and of A-51568B) of the N—CH$_3$ resonance for N-(methyl)leucine present in the spectrum of Vancomycin B. Thus, the proton nmr spectrum of Vancomycin B contains a methyl singlet at 2.34 ppm, which is absent from the proton nmr spectrum of antibiotic A-51568. The chief difference between the proton nuclear magnetic resonance spectrum of A-51568 and A-51568B is the absence in the spectrum of A-51568B of the asparagine resonances found in A-51568 (and also in Vancomycin B) and replacement thereof by the glutamine resonances of A-51568B.

Although no stereochemical assignments are indicated in the structures given herein, the stereochemistry of A-51568 at the chiral centers is identical to that of Vancomycin B.

Based on the molecular weight, the proton nuclear magnetic resonance spectrum data, and the elemental analysis, an empirical formula of $C_{65}H_{73}Cl_2N_9O_{24}$ is assigned to antibiotic A-51568.

Potentiometric titration of antibiotic A-51568 in 66 percent aqueous dimethylformamide indicated pKa values of ~6.2, 8.8, 10.3, and 12.85 (initial pH=6.12).

Antibiotic A-51568 has the following specific rotation: $[\alpha]_D^{25°}$ C.=−20.4° (C=10 mg/ml, water), $[\alpha]_{365}^{25°}$ C.=−33.6° (C=10 mg/ml, water).

Figure 1:
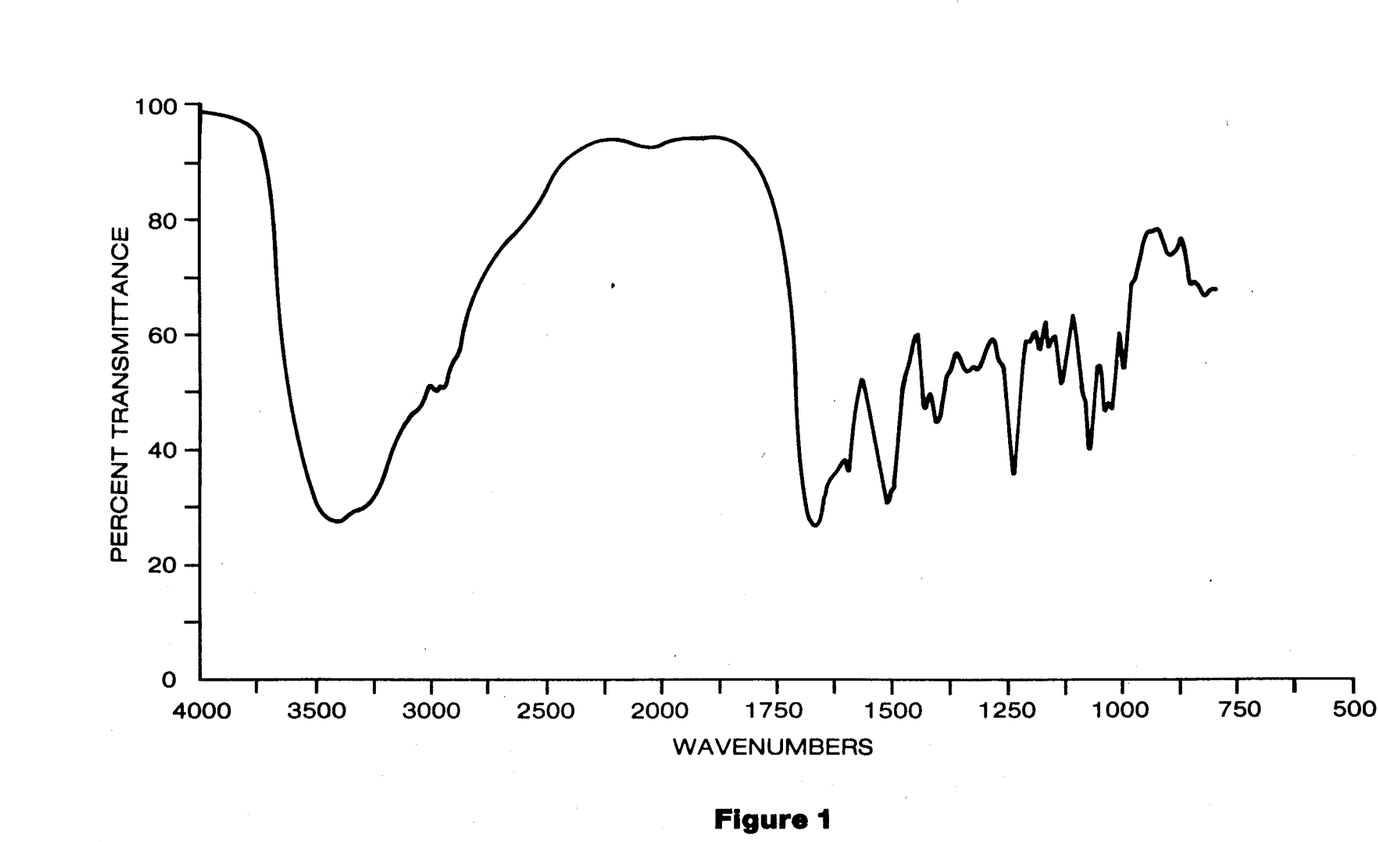

The infrared absorption spectrum of antibiotic A-51568 in KBr pellet is shown in the accompanying drawing as FIG. 1. The following distinguishable absorption maxima are observed: 3400 (broad, strong), 3380 (broad, strong), 1657 (broad, strong), 1587 (medium strong), 1505 (medium strong), 1424 (medium), 1396 (medium), 1328 (broad, weak), 1310 (broad, weak), 1231 (medium strong), 1174 (weak), 1156 (weak), 1128 (medium), 1062 (medium strong), 1028 (weak), 1015 (weak), 990 (weak), 882 (weak), 881 (weak) cm$^{-1}$.

The ultraviolet absorption maxima of antibiotic A-51568 in water under acid, neutral, and basic conditions are recorded in Table 2, which follows.

TABLE 2

UV Spectrophotometry of Antibiotic A-51568

| Acid or Neutral max nm (ε) | Basic max nm (ε) |
|---|---|
| 278 (5,500) | 302 (6,000) |
| 234 (shoulder) (25,000) | 264 (shoulder) (10,000) |

The antibiotic substance of this invention is arbitrarily designated herein as the A-51568 antibiotic.

The A-51568 antibiotic substance is produced by culturing a hitherto undescribed strain of the species *Nocardia orientalis*. This strain is referred to herein as *Nocardia orientalis* NRRL 15232 or the A-51568.1 strain.

This invention further relates to the biologically pure culture of the hitherto undescribed strain of *Nocardia orientalis* NRRL 15232. For convenience, this culture has been designated in our laboratory as culture A-51568.1.

Culture A-51568.1 is a variant strain derived through natural selection from culture A-51568, which latter culture was initially isolated from a soil sample collected in Yucatan, Mexico.

Culture A-51568.1 is classified as a strain of *Nocardia orientalis* based on simultaneous laboratory comparisons, as well as comparison with the published descriptions of Nocardia by D. Berd, "Laboratory Identification of Clinically Important Aerobic Actinomycetes", *Appl. Microbiol.* 25(4), 665–681 (1973); by Bergey's Manual of Determinative Bacteriology, 8th Edition, edited by R. E. Buchanan and N. E. Gibbons (The Williams and Wilkins Co., Baltimore); by R. E. Gordon et al., "*Nocardia coeliaca, Nocardia autotrophia,* and the Nocardin Strain", *Int. J. Syst. Bacteriol.* 24(1), 54–63 (1974); by R. E. Gordon et al., "Resistance to Rifampin and Lysozyme of Strains of Some Species of Mycobacterium and Nocardia as a Taxonomic Tool", *Int. J. Syst. Bacteriol.* 27(3), 176–178 (1977); by S. A. Waksman, The Actinomycetes Vol. II, [The Williams and Wilkins Co., Baltimore (1961)]; and with the published descriptions of this species by R. E. Gordon et al., "Some Bits and Pieces of the Genus Nocardia: *N. carnea, N. vacinii, N. transvalensis, N. orientalis,* and *N. aerocolonigenes*", *J. Gen. Microbiol.* 109, 69–78 (1978); by S. J. Mishra et al., "Identification of Nocardiae and Streptomycetes of Medical Importance", *J. Clin. Microbiol.* 11(6), 728–736 (1980); and by Pittenger et al., "*Streptomyces orientalis,* n. sp., the Source of Vancomycin", *Antibiot. and Chemoth.* VI(11), 642–647 (1956).

The methods and media recommended for the International Streptomyces Project (ISP) for the characterization of Streptomyces species, as published by Shirling and Gottlieb ["Methods of Characterization of Streptomyces Species", *Int. J. Syst. Bacteriol.* 16(3), 313-340 (1966)], as well as methods recommended for the characterization of Nocardia species, as published by Gordon et al., "*Nocardia coeliaca, Nocardia autotrophia,* and the Nocardin Strain", *Int. J. Syst. Bacteriol.* 24(1), 54-63 (1974) were followed.

CHARACTERIZATION OF A-51568.1 CULTURE

Morphology

Culture A-51568.1 produces an extensive substrate and aerial mycelium. When viewed under the light microscope, the aerial hyphae have a cobweb-like appearance. When grown under submerged, shaken conditions, the hyphae break into short mycelial fragments.

No conidia were observed when aerial hyphae were viewed by light microscopy. However, conidia are seen when studied by scanning electron microscopy. These features are observed when culture A-51568.1 is grown on ISP medium No. 5 and tap water agar. The spore surface ornamentation is smooth (Sm). The spore shape is spherical to cylindrical, and the spores are poorly and irregularly formed. This morphology is classified in the nonstreptomycetes section as described in Bergey's Manual, supra.

Cultural Characteristics

Culture A-51568.1 grew well on yeast dextrose agar, as well as on many other agar media, the growth being often wrinkled and flaky. Abundant aerial mycelia were produced having a spore mass color in the gray (GY) and sometimes white (W) color series. The nearest matching color tab for the gray color series in the Tresner and Backus system [see Tresner and Backus, "System of Color Wheels for Streptomycete Taxonomy", *Appl. Microbiol.* 11, 335-338 (1956)] is d light Gray to 2dc yellowish Gray.

The aerial growth is neither as dense nor as long as typical Streptomyces. The aerial growth is produced on inorganic salts-starch agar (ISP No. 4), on glycerol-asparagine agar (ISP No. 5), and glycerol-glycine agar, and is best observed when grown on yeast-malt extract agar (ISP No. 2).

A dark brown distinctive color is observed on the reverse side in the following agar media: ISP No. 2, ISP No. 5, tyrosine agar (ISP No. 7), and glycerol-glycine agar. This color is unaffected by pH. A light to reddish brown soluble pigment is also elaborated in the above-named media, as well as in Czapek's solution agar and in glucose-asparagine agar. The reverse color of culture A-51568.1 in other media is yellow-brown.

When plated for variability, culture A-51568.1 showed no mixture of colony types, and culture A-51568.1 is therefore regarded as a stable isolate.

The cultural characteristics of culture A-51568.1 on various media compared with the cultural characteristics of *Nocardia orientalis* ATCC 19795 are presented in Table 3, which follows.

Color names were assigned according to the ISCC-NBS Centroid Color Charts Sample No. 2106 (National Bureau of Standards, U.S. Department of Commerce, 1958), and the Color Harmony Manual, 4th Edition (Color Standards Department, Container Corporation of America, Chicago, Ill., 1958).

TABLE 3

Growth Characteristics of A-51568.1 and ATCC 19795 on Various Media

| Medium | A-51568.1 | ATCC 19795 |
| --- | --- | --- |
| ISP 2 | G: Abundant-wrinkled surface | Abundant-wrinkled surface |
| | R: 59.d.Br (no pH change) | 72.d.OY |
| | Am: Abundant:d 1. Gray (GY) | Abundant:2ba pale Yellow (Y) |
| | Sp: Reddish-brown | None |
| ISP 3 | G: Abundant | Abundant |
| | R: 89.p.Y | 89.p.Y |
| | Am: Good:d 1.Gray (GY) | Good:d 1.Gray (GY) |
| | Sp: None | None |
| ISP 4 | G: Abundant | Abundant |
| | R: 72.d.OY | 70.1.OY |
| | Am: Abundant:b Oyster White (W) | Abundant:b Oyster White (W) |
| | Sp: None | None |
| ISP 5 | G: Abundant | Abundant |
| | R: 59.d.Br (no pH change) | 70.1.OY |
| | Am: Abundant:b Oyster White (W) | Abundant:b Oyster White (W) |
| | Sp: Light Brown | None |
| ISP 7 | G: Abundant | Abundant |
| | R: 65.br.Black (no pH change) | 71.m.OY |
| | Am: Abundant:2ba p. Yellow (Y) | Abundant:2ba p. Yellow (Y) |
| | Sp: Dark reddish-brown | None |
| Czapeks Solution | G: Good | Good |
| | R: 74.s.yBR | 70.1.OY |
| | Am: Good:b Oyster White (W) | Good:b Oyster White (W) |
| | Sp: Light brown | None |
| Emerson's Agar | G: Abundant-wrinkled, flaky | Abundant-wrinkled, flaky |
| | R: 74.s.yBr | 74.s.yBr |
| | Am: Good:d.1.GYT 2ba p.Y (GY) | Good:2ba p. Yellow (Y) |
| | Sp: None | None |
| Glucose Asparagine | G: Abundant | Abundant |
| | R: 75. deep γBr | 67. brill.OY |
| | Am: Abundant:2dc y Gray (GY) | Abundant:2ba p. Yellow (Y) |
| | Sp: Olive-brown | None |
| Glycerol-glycine | G: Abundant | Abundant |
| | R: 78.d.yB (no pH change) | 71.m.OY |
| | Am: Abundant:2dc y Gray (GY) | Abundant:2ba p. Yellow (Y) |
| | Sp: Olive-brown | None |
| Nutrient Agar | G: Good | Good |
| | R: 70.1.OY | 70.1.OY |
| | Am: Good:b Oyster White (W) | Good:b Oyster White (W) |
| | Sp: None | None |
| Tap H₂O | G: Fair | Fair |
| | R: 93.γ Gray | 93. γ Gray |
| | Am: Poor | Poor |
| | Sp: None | None |
| Yeast Dextrose | G: Abundant-wrinkled, flaky | Abundant-slightly wrinkled |
| | R: 68.s.OY | 68.s.OY |
| | Am: Abundant:d light Gray (GY) | Abundant:b Oyster White (W) |
| | Sp: None | None |

G = growth
R = reverse
Am = aerial mycelia
Sp = soluble pigment

Cell Wall Studies

Using hydrolyzed whole cells of A-51568.1 culture, the presence of certain diagnostic sugars was determined by the chromatographic method of M. P. Lechevalier, "Identification of Aerobic Actinomycetes of Clinical Importance", *J. Lab. Clin. Med.* 71, 931-944 (1968).

Hydrolyzed whole cells were used to determine the isomers of diaminopimelic acid according to the method of Becker et al., *Appl. Microbiol.* 11, 421–423 (1964).

The results of these studies are set forth below.

In addition to the above determinations, culture A-51568.1 was studied and compared with published data on 21 *N. orientalis* reference strains, as well as simultaneous comparisons with NRRL 2451, NRRL 2452, and ATCC 19795. The comparison of the cultural, morphological, and physiological properties is recorded in Table 4, which follows.

TABLE 4

Comparison of Physiological Properties of A-51568.1 and *N. orientalis* Reference Strains

| Characteristic | A-51568.1 | NRRL 2451 | NRRL 2452 | ATCC 19795 | *N. orientalis* |
|---|---|---|---|---|---|
| Acid-fastness | − | − | − | − | − |
| Aerial hyphae | + | + | + | + | + |
| Catalase | + | + | + | + | + |
| Cell wall type | IV | IV | IV | IV | IV |
| Conidia | + | + | + | + | + |
| Decomposition of | | | | | |
| adenine | − | − | − | − | − |
| casein | + | + | + | + | + |
| DNA | + | + | + | + | ND |
| hypoxanthine | + | + | + | + | + |
| tyrosine | + | + | + | + | + |
| urea | + | + | + | + | + |
| xanthine | + | + | + | − | − |
| Fragmentation | + | + | + | + | + |
| Galatin liquefaction | + | + | + | + | ND |
| Gram Stain | + | + | + | + | ND |
| Hydrolysis of: | | | | | |
| esculin | + | + | + | + | + |
| hippurate | + | + | + | + | + |
| skim milk | + | + | + | + | + |
| starch | + | + | + | + | + |
| Melanoid pigmentation | − | − | − | − | ND |
| Morphology - cobweb | + | + | + | + | + |
| NaCl tolerance-% | 8 | 8 | 8 | 10 | ND |
| Nitrite from nitrate | − | − | − | + | − |
| Phosphatase | + | + | + | + | ND |
| Resistance to | | | | | |
| bacitracin | − | − | − | − | ND |
| lysozyme | + | + | + | + | − |
| novobiocin | − | − | − | + | ND |
| penicillin G | + | + | + | + | ND |
| rifampin | + | + | + | + | + |
| Spore color | GY-W | W-Y | W-Y | W-Y | W-Y |
| Spore shape spherical to cylindrical | + | + | + | + | + |
| Spore surface, smooth | + | + | + | + | + |
| Survival at 50° C., 8h | + | + | + | + | + |
| Temperature range, °C. | 10–40 | 15–40 | 15–40 | 10–40 | 10–40 |
| Type A sugar pattern | + | + | + | + | + |
| Urease production | + | + | + | + | + |
| Utilization pattern of carbon compounds | + | + | + | + | + |
| Utilization pattern of organic acids | + | + | + | + | + |
| Vegetative growth optimum in the same medium | + | + | + | + | ND |

ND = not done

| Test | Result Observed |
|---|---|
| Diagnostic sugars | Galactose, Arabinose, Ribose |
| Isomers of 2,6-diaminopimelic acid | Meso-isomer |

These results represent a Type A whole-cell sugar pattern, and a Type IV cell wall, which combination of major cell wall constituents is indicative of the genus Nocardia. See M. P. Lechevalier, supra.

Using thin-layer chromatography of whole-cell methanolysates, according to the method described by D. E. Minnikin et al., "Differentiation of Mycobacterium, Nocardia, and Related Taxa by Thin-layer Chromatographic analysis of Whole-organism Methanolysates," *J. Gen. Microbiol.* 88, 200–204 (1975), no mycolic acid methyl esters were observed.

Further, the acid production from carbohydrates by cultures A-51568.1, NRRL 2451, NRRL 2452, and ATCC 19795 was compared with the published results of 21 *N. orientalis* reference strains. This information is recorded in Table 5, which follows.

TABLE 5

Acid Production From Carbohydrates by Cultures A-51568.1, NRRL 2451, NRRL 2452, ATCC 19795, and *N. orientalis* Reference Strains

| Characteristic | A-51568.1 | NRRL 2451 | NRRL 2452 | ATCC 19795 | *N. orientalis* |
|---|---|---|---|---|---|
| Adonitol | − | + | + | + | + |
| l(+) Arabinose | + | + | + | + | + |
| Cellobiose | + | + | + | + | + |
| Cellulose | − | − | − | − | ND |
| Dulcitol | − | − | − | − | ND |

TABLE 5-continued

Acid Production From Carbohydrates by Cultures A-51568.1, NRRL 2451, NRRL 2452, ATCC 19795, and N. orientalis Reference Strains

| Characteristic | A-51568.1 | NRRL 2451 | NRRL 2452 | ATCC 19795 | N. orientalis |
|---|---|---|---|---|---|
| i-Erythritol | + | + | + | + | + |
| Fructose | + | + | + | + | ND |
| d(+) Galactose | + | + | + | + | ND |
| Glucose | + | + | + | + | + |
| Glycerol | + | + | + | + | + |
| i-Inositol | + | + | + | + | + |
| Inulin | + | + | + | + | ND |
| d(+) Lactose | + | + | + | + | + |
| d(+) Maltose | + | + | + | + | + |
| d(−) Mannitol | + | + | + | + | + |
| d(+) Mannose | + | + | + | + | + |
| d(+) Melezitose | + | + | + | − | − |
| d(+) Melibiose | − | − | − | − | − |
| α-Me-D-Glucoside | + | + | + | + | + |
| d(+) Raffinose | − | − | − | − | − |
| l(+) Rhamnose | − | − | − | + | − |
| Salicin | + | + | + | + | ND |
| d(−) Sorbitol | − | − | − | − | − |
| Sucrose | + | + | + | + | ND |
| d(+) Trehalose | + | + | + | + | + |
| d(+) Xylose | + | + | + | + | + |
| Control | − | − | − | − | − |

ND = not done

Using the cultural, morphological, and physiological characteristics determined for A-51568.1, comparison was made with the published descriptions of 14 taxa of Nocardia, as published by R. E. Gordon et al., "Some Bits and Pieces of the Genus Nocardia: N. carnea, N. vaccinii, N. transvalensis, N. orientalis, and N. aerocolonigenes", J. Gen. Microbiol. 109, 69–78 (1978); and by S. J. Mishra et al., "Identification of Nocardia and Streptomycetes of Medical Importance", J. Clin. Microbiol. 11(6), 728–736 (1980). In addition, simultneous laboratory comparisons were made between culture A-51568.1 and cultures NRRL 2451, NRRL 2452, and ATCC 19795.

Similarity coefficients were then calculated from the equation $$S = [Ns^+ + Ns^-]/[Ns^+ + Ns^- + Nd] \times 100$$

where
Ns+ = number of positive similarities
Ns− = number of negative similarities
Nd = number of dissimilarities (differences)

See: W. A. Kurylowicz et al., "Numerical Taxonomy of Streptomycetes", Polish Medical Publishers, Warsaw (1975).

The properties used to calculate similarity coefficients were mainly physiological characteristics. Comparisons were made by measuring all the other strains against culture A-51568.1. Thus, A-51568.1 compared to itself was rated as 100. The comparisons are recorded in Table 6, which follows.

TABLE 6

Coefficient of Similarity Between Culture A-51568.1 and Several Nocardia Reference Strains

| Culture | Coefficient |
|---|---|
| A-51568.1 | 100 |
| NRRL 2451 | 95 |
| NRRL 2452 | 95 |
| ATCC 19795 | 86 |
| N. orientalis (composite of 21 strains) | 89 |

TABLE 6-continued

Coefficient of Similarity Between Culture A-51568.1 and Several Nocardia Reference Strains

| Culture | Coefficient |
|---|---|
| N. aerocolonigenes | 76 |
| N. hirsuta | 68 |
| N. autotrophia | 65 |
| N. dassonvillei | 63 |
| N. madurea | 63 |
| N. brasiliensis | 61 |
| N. caviae | 61 |
| N. transvalensis | 57 |
| N. amarae | 53 |
| N. vaccinii | 50 |
| N. asteroides | 47 |
| N. carnea | 47 |
| N. pelletieri | 39 |

A comparison of the similarities and differences between culture A-51568.1 and N. orientalis ATCC 19795 is set forth in Table 7, which follows.

TABLE 7

Similarities and Differences of Culture A-51568.1 and culture ATCC 19795

| Similarities | Differences |
|---|---|
| Acid from carbohydrates | Cultural characteristics on some media: |
| Aerial hyphae | aerial mycelia color |
| Catalase production | reverse color |
| Cell wall type IV | soluble pigmentation |
| Conidia present | Decomposition of xanthine |
| Cultural characteristics | NaCl tolerance |
| Decomposition of: | Nitrate reduction |
| casein | Resistance to novobiocin |
| DNA | |
| hypoxanthine | |
| tyrosine | |
| Fragmentation of mycelium | |
| Gelatin liquefaction | |
| Hydrolysis of: | |
| esculin | |
| hippurate | |
| skim milk | |
| starch | |
| Inability to decompose adenine | |
| Melanoid pigments absent | |
| Morphology | |
| Phosphatase production | |
| Resistance to: | |
| lysozyme | |
| penicillin | |
| rifampin | |
| Sensitivity to bacitracin | |
| Spore shape | |
| Spore surface ornamentation | |
| Staining reaction | |
| Sugar pattern of whole cell hydrolysates type A | |
| Survival at 50° C. for 8 hrs. | |
| Temperature range (10–40° C.) | |
| Urease production | |
| Utilization of organic compounds | |
| Vegetative growth in CSM medium | |

Culture A-51568.1 has been deposited and made a part of the stock culture collection of the Northern Regional Research Center, U.S. Department of Agriculture, Agricultural Research Service, Peoria, Ill. 61604, from which it is available to the public under the accession number NRRL 15232.

Also a part of this invention are the pharmaceutically-acceptable, non-toxic salts of antibiotic A-51568. "Pharmaceutically-acceptable" salts are salts in which the toxicity of the compound as a whole toward warmblooded animals is not increased relative to the non-salt form. Representative and suitable salts of antibiotic A-51568 include those acid addition salts formed by standard reaction with both organic and inorganic acids such as, for example, sulfuric, phosphoric, hydrochloric, acetic, succinic, citric, lactic, maleic, fumaric palmitic, cholic, pamoic, mucic, D-glutamic, d-camphoric, glutaric, glycolic, phthalic, tartaric, formic, lauric, stearic, salicylic, methansulfonic, benzenesulfonic, sorbic, picric, benzoic, cinnamic and the like acids; as well as those salts formed by the carboxyl group with strong bases such as sodium hydroxide, potassium hydroxide, sodium carbonate, potassium carbonate, ammonium hydroxide, diethanolamine, and like bases.

The activity of antibiotic A-51568 against a variety of bacteria, as determined by the agar-dilution method, is reported in the following Table 8, wherein the minimum inhibitory concentration (MIC) values are recorded.

TABLE 8
ACTIVITY OF A-51568 AGAINST A VARIETY OF BACTERIA

| Bacteria | MIC ($\mu$g./ml.) |
|---|---|
| *Staphylococcus aureus* | |
| 3055* | 0.5 |
| X400 | 1 |
| V138 | 1 |
| V140 | 1 |
| V102 | 1 |
| *Staphylococcus epidermidis* | |
| 222 | 1 |
| 270 | 2 |
| 285 | 2 |
| 219 | 1 |
| 269 | 2 |
| *Streptococcus pyogenes* | |
| C203 | 0.5 |
| ATCC 10389 | 0.5 |
| *Streptococcus sp. Group B* | |
| 5 | 4 |
| 14 | 0.5 |
| *Streptococcus sp. Group D* | |
| X66 | 1 |
| 9960 | 4 |
| 2041 | 2 |
| 8043 | 1 |
| 9901 | 2 |
| 12253F | 1 |
| Mx161 | 1 |
| 2058 | 4 |
| *Streptococcus pneumoniae* | |
| Park I | 0.125 |
| Bl-438 | 0.5 |
| *Haemophilus parainfluenzae* | |
| 7901 | 64 |
| 9796 | 64 |
| *Haemophilus influenzae* | |
| C.L. | 32 |
| Mx366 | 32 |
| Mx371 | 64 |
| 76 | 64 |
| Bond | 64 |
| 16836 | 128 |
| 4842 | 32 |
| 312 | 128 |

*The name or number appearing under each organism identifies the strain of the organism employed in the test.

The in vitro activity of antibiotic A-51568 against a number of aerobic bacteria has been determined using a standard agar-dilution assay. The results, determined by reading the end point after 24 hours, are recorded in the following Table 9.

TABLE 9
ACTIVITY OF A-51568 AGAINST AEROBIC BACTERIA

| Test Organism | MIC ($\mu$g./ml.) |
|---|---|
| *Staphylococcus aureus* 3055 | 1 |
| *Staphylococcus aureus* V41 | 1 |
| *Staphylococcus aureus* X400 | 2 |
| *Staphylococcus aureus* S13E | 1 |
| *Staphylococcus epidermidis* EPI1 | 2 |
| *Staphylococcus epidermidis* EPI2 | 1 |
| *Streptococcus pyogenes* C203 | 1 |
| *Streptococcus pneumoniae* Park I | 0.5 |
| Streptococcus sp. Group D X66 | 1 |
| Streptococcus sp. Group D 9960 | 4 |
| *Haemophilus influenzae* (sensitive) Holt | 64 |
| *Haemophilus influenzae* (resistant) R252 | 128 |
| *Escherichia coli* N10 | >128 |
| *Escherichia coli* EC14 | >128 |
| *Escherichia coli* TEM | 128 |
| *Klebsiella pneumoniae* X26 | >128 |
| *Klebsiella pneumoniae* KAE | >128 |

Antibiotic A-51568 has been tested and found to be active against a number of anaerobic bacteria, as recorded in the following Table 10 the MIC values having been determined by the agar-dilution method.

TABLE 10
ACTIVITY OF A-51568 AGAINST ANAEROBIC BACTERIA

| Test Organism | MIC ($\mu$g./ml.) |
|---|---|
| *Clostridium difficile* 2994 | 2 |
| *Clostridium perfringens* 81 | 1 |
| *Clostridium septicum* 1128 | 1 |
| *Eubacterium aerofaciens* 1235 | 2 |
| *Peptococcus asaccharolyticus* 1302 | 16 |
| *Peptococcus prevoti* 1281 | 32 |
| *Peptostreptococcus anaerobius* 1428 | 1 |
| *Peptostreptococcus intermedius* 1264 | 1 |
| *Propionibacterium acnes* 79 | 1 |
| *Bacteroides fragilis* 111 | 32 |
| *Bacteroides fragilis* 1877 | 32 |
| *Bacteroides fragilis* 1936B | 32 |
| *Bacteroides thetaiotaomicron* 1438 | 32 |
| *Bacteroides melaninogenicus* 1856/28 | >128 |
| *Bacteroides melaninogenicus* 2736 | 16 |
| *Bacteroides vulgatis* 1211 | 32 |
| *Bacteroides corrodens* 1874 | 32 |
| *Fusobacterium symbiosum* 1470 | 2 |
| *Fusobacterium necrophorum* 6054A | 2 |

Antibiotic A-51568 is also active against a number of strains of *Clostridium difficile*, as determined by the agar-dilution method. The results of the tests are recorded in the following Table 11.

TABLE 11
ACTIVITY OF ANTIBIOTIC A-51568 AGAINST *CLOSTRIDIUM DIFFICILE* STRAINS

| Clostridium difficile | MIC ($\mu$g./ml.) |
|---|---|
| 8484 | 2 |
| 6890 | 2 |
| 2634 | 2 |
| 78 | 2 |
| A-194 | 2 |
| A-195 | 2 |
| A-196 | 2 |
| A-279 | 2 |
| A-280 | 2 |
| A-281 | 2 |
| WAL-2112 | 2 |
| WAL-3657 | 2 |
| WAL-4268 | 2 |
| 107B | 2 |
| 111F | 2 |
| 1153 | 2 |
| 3424-5B | 2 |

TABLE 11-continued
ACTIVITY OF ANTIBIOTIC A-51568 AGAINST *CLOSTRIDIUM DIFFICILE* STRAINS

| *Clostridium difficile* | MIC (µg./ml.) |
|---|---|
| 3816 | 2 |
| 3950D | 2 |

Antibiotic A-51568 has shown in vivo antimicrobial activity against experimental bacterial infections. When two doses of test compound were administered subcutaneously to mice in illustrative infections, the activity observed is measured as an $ED_{50}$ [effective dose in mg/kg to protect fifty percent of the test animals: See Warren Wick et al., *J. Bacteriol.* 81, 233–235 (1961)]. The $ED_{50}$ values observed for antibiotic A-51568 are as follows:

*S. aureus* 3055 1.79 mg/kg×2
*S. pyogenes* C203 3.03 mg/kg×2
*S. pneumoniae* Park I 2.71 mg/kg×2

In one of its aspects this invention provides a method for treating infections in man or animals which comprises administering to said man or animal a non-toxic antibiotic-effective dose of between about 25 mg. and about 2,000 mg. of antibiotic A-51568, or a pharmaceutically-acceptable, non-toxic salt of the antibiotic.

In the treatment of infections in man, the antibiotic is administered by the parenteral route, e.g., by i.m. injection, or i.v. infusion. For injection, the antibiotic, or a pharmaceutically-acceptable diluent at the desired concentration is administered. Suitable diluents include, for example, Water-for-Injection, 0.9% saline, 5% dextrose, Ringer's solution, or other commonly employed diluent. For administration by i.v. infusion, the antibiotic or salt thereof can be made up in a physiological fluid or dilute nutrient at a suitable concentration; for example, at a concentration between about 5% and about 10%, and slowly infused with the fluid. Alternatively, the antibiotic may be administered by the "piggy-back" method.

The antibiotic, or the pharmaceutically-acceptable, non-toxic salts thereof can be made up in dosage unit formulations in hermetically sealed vials, sterile, rubber-stoppered vials, or in plastic pouches. Such unit dosage forms can contain excipients such as antioxidants, solubilizing agents, dispersing agents, buffers, and the like. One such dosage unit formulation comprises 100 mg. of A-51568 antibiotic, or a pharmaceutically-acceptable, non-toxic salt thereof, in a rubber (butyl rubber) stoppered vial. Another dosage unit formulation comprises 250 mg. of antibiotic A-51568, or a salt thereof, in a sterile, sealed vial. For i.v. infusion, a dosage unit formulation of this invention comprises 5 g. of antibiotic A-51568, or a pharmaceutically-acceptable, non-toxic salt thereof, in a plastic pouch.

When antibiotic A-51568 is used as an antibacterial agent, it may be administered either orally or parenterally. As will be appreciated by those skilled in the art, the A-51568 antibiotic is commonly administered together with a pharmaceutically-acceptable carrier or diluent. The dosage of A-51568 antibiotic will depend upon a variety of considerations, such as, for example, the nature and severity of the particular infection to be treated. Those skilled in the art will recognize that appropriate dosage ranges and/or dosage units for administration may be determined by considering the MIC and $ED_{50}$ values herein provided, together with factors such as the patient or host, and the infecting organism.

The A-51568 antibiotic is useful inter alia for suppressing the growth of Staphylococcus, Streptococcus, and *Propionibacterium acnes* organisms, and the antibiotic could therefore be used, for example, in the treatment of acne. The A-51568 antibiotic, in purified state, can be formulated in pharmaceutically-acceptable diluents such as isopropyl alcohol for application to the skin. Such solutions can be made up with antibiotic concentrations of from about 1 to about 15 percent weight per volume. Alternatively, the antibiotic can be made up into creams or lotions for application to the skin.

Antibiotic A-51568 is also useful for suppressing the growth of *Clostridium difficile* organisms, which cause pseudomembranous colitis in the intestine. The A-51568 antibiotic could therefore be used in the treatment of pseudomembranous colitis by the oral administration of an effective dose of the antibiotic or a pharmaceutically-acceptable, non-toxic salt thereof, prepared in a pharmaceutically-acceptable dosage form. For such use the A-51568 antibiotic can be administered in gelatin capsules or in liquid suspension.

The antibiotics A-51568 and A-51568B are co-produced by culturing the previously undescribed microorganism *Nocardia orientalis* NRRL 15232, or an A-51568 and/or A-51568B-producing mutant or varient thereof, in a culture medium containing assimilable sources of carbon, nitrogen, and inorganic salts, under submerged aerobic fermentation conditions until a substantial level of antibiotic activity is produced.

A number of different media may be used in culturing *Nocardia orientalis* NRRL 15232 to produce the A-51568 and B antibiotics. For economy in production, optimal yield, and ease of product isolation, however, certain culture media are preferred. These media should contain assimilable sources of carbon, nitrogen, and inorganic salts. Suitable carbon sources include potato dextrin, glycerol, soluble starch, glucose, galactose, lactose, maltose, and refined soybean oil. Optimum levels of carbon sources are from about 2 to about 5 percent by weight. Potato dextrin and soluble starch are the more preferred carbon sources.

Preferred nitrogen sources include sodium glutamate, meat peptone, sodium nitrate, ammonium nitrate, ammonium sulfate, soybean grits, and yeast. Meat peptone (e.g., Bacto-peptone (Difco Laboratories)) is the more preferred nitrogen source.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium, calcium, ammonium, chloride, carbonate, phosphate, sulfate, nitrate and like ions.

To increase production of the antibiotic mixture, various biosynthetic precursors can be added to the fermentation medium. For example, p-hydroxyphenylglycine can be added to the medium at the level of $5 \times 10^{-3}$M. Such addition was found in one experiment to increase productivity by 64%. Similar, but less spectacular increases in yield were observed by the addition of tyrosine (14%), p-hydroxyphenylglyoxylic acid (27%) and L-leucine (18%) at the same level as p-hydroxyphenylglycine. The addition of shikimic acid had no effect on the yield of the complex, while the addition of L-asparagine and L-glutamine had no significant effect on the yield.

Productivity of the antibiotic is also affected by phosphate levels. Enrichment of phosphate by as little as $3 \times 10^{-4}$M (0.05 mg/ml) was found in one experiment to depress yields by 20%.

It may be necessary to add small amounts (i.e., 0.2 ml/L) of an antifoam agent such as propylene-glycol to large-scale fermentation media if foaming becomes a problem.

The A-51568 and B-producing organism can be grown over a broad temperature range of from about 25° to about 37° C. Optimum production of the A-51568 antibiotic was originally thought to be about 30° C. but was subsequently found to be about 32° to 34° C.

Although small quantities of the A-51568 and Factor B antibiotics may be obtained by shake-flask culture, submerged aerobic fermentation in tanks is preferred for producing substantial quantities of the antibiotics. For tank fermentation, it is preferable to use a vegetative inoculum. The vegetative inoculum is prepared by inoculating a small volume of culture medium with the spore form, or mycelial fragments, to obtain a fresh, actively growing culture of the organism. The vegetative inoculum is then transferred to a larger tank where, after a suitable incubation time, the A-51568 and A-51568B antibiotics are produced in optimal yield.

An alternate method of providing inoculum for the vegetative medium consists of substituting a lyophilized pellet for the aqueous spore suspension. Lyophilized pellets are prepared in a manner known in the art. Preparation of the spore suspension for lyophilization is similar to the preparation of the aqueous spore suspension, except that sterile calf serum is substituted for sterile distilled water.

As is customary in aerobic submerged culture processes, sterile air is dispersed through the culture medium. For efficient growth of the organism, the volume of air used in tank production is in the range of from about 0.1 to about 0.25 volumes of air per volume of culture medium per minute (v/v/m), with from about 100 to about 300 RPM agitation. An optimum rate in a 165-liter vessel containing 110 liters of fermentation medium is about 0.125 v/v/m, with agitation provided by impellers rotating at about 200 RPM.

The level of antibiotic activity in the fermentation medium is determined by the following assay. A whole broth sample is centrifuged for about 15 minutes at $1000 \times g$, and the centrate removed for assay. The antibiotic activity is present in the supernatant. The assay is done microbiologically by an agar well plate test employing *Micrococcus luteus* ATCC 9341.

Production of the A-51568 and B antibiotics also can be monitored during the fermentation by either agar diffusion using *Bacillus subtilis* ATCC 6633, or a turbidimetric method using *Staphylococcus aureus* ATCC 9114.

Antibiotic activity is generally present after about 24 hours and remains present for at least 168 hours during the fermentation period. Peak antibiotic production occurs at from about 90 hours to about 114 hours fermentation time.

Factor B is then ultimately separated from A-51568 by chromatography of the filtered fermentation broth. Most of the antibiotic activity is found in the broth, while minor amounts of antibiotic activity may be associated with the mycelia. The A-51568 and B antibiotics are most readily separated from the fermentation mixture by removal of the mycelia, i.e., the biomass, by filtration. The antibiotics are then isolated from the filtered fermentation broth, preferably by column chromatography over a suitable adsorbent using an appropriate eluting agent.

Suitable adsorbents include carbon, anion and cation exchange resins, polyamide, carboxymethylcelluloses, highly porous copolymers of styrene and divinylbenzene such as Diaion HP-20, the Amberlite XAD resins, the Ionac resins, hydrophilic, insoluble, molecular-sieve chromatographic media made by cross-linking dextran such as the Duolite resins, and also TSK Gels. The Diaion resins are a product of Mitsubishi Chemical Industries, Limited, Tokyo, Japan. The Amberlite XAD resins are produced by Rohm and Haas, Philadelphia, Pa. Ionac resins are available from Ionac Chemical Co., a division of Sybron Corporation, Birmingham, N.J. The Duolite resins are products of Diamond Shamrock, Redwood City, Calif. Sephadex resins are manufactured by Pharmacia Fine Chemicals AB, Uppsala, Sweden. The TSK Gels are available from E. Merck, Darmstadt, Germany, and from Bio-Rad, 2200 Wright Ave., Richmond, Calif., 94804.

In order to illustrate more fully the operation of this invention, the following Examples are provided. Examples 1 through 3 form one set and teach the isolation of A-51568. Examples 4 through 7 form the second set and teach the isolation of A-51568 and A-51568B from a large amount of fermentation broth.

In the following Examples 5, 6, and 7 the antibiotic activity of each of the collected fractions is tested using a *M. luteus* disc plate assay.

The relative amount of antibiotic activity in each fraction of Examples 5, 6 and 7 is estimated by a bioassay wherein the activity of various dilutions of the fraction are compared to various dilutions of vancomycin on a disc plate assay using *M. luteus* as the test organism. The fractions are diluted and the vancomycin is dissolved in pH 6 buffer then diluted. A standard vancomycin solution is also run with each dilution. It is assumed that A-51568 and A-51568B have the same MIC against the test organisms as does vancomycin. Thus, when the zone of inhibition sizes between the fraction dilution and the vancomycin dilution are approximately the same, the amount of A-51568 and A-51568B present in the fraction can be calculated from the known concentration of vancomycin.

Finally, in Examples 5, 6 and 7 the degree of separation of A-51568 and A-51568B from other components and ultimately from each other is monitored by the use of high performance liquid chromatography (HPLC). The HPLC system used to monitor the progress of the other chromatography steps (Examples 5 and 6) is then used to separate A-51568 and A-51568B (Example 7).

Specifically, the HPLC system consists of an $8 \times 150$ mm Waters Associates Nova Pac RCM reversed phase column using an eluant flow rate of approximately 2 ml/minute at 900 p.s.i. The u.v. detector is set at 230 nm. The eluant is composed of two solvent solutions, solution A being an aqueous solution of 2% methanol, 1% tetrahydrofuran, 0.5% triethylamine (buffer) with the pH of the solution adjusted to 3.2 by the addition of phosphoric acid. Solution B is an aqueous solution of 40% methanol, 1% tetrahydrofuran, 0.5% triethylamine (buffer) with the pH of the solution adjusted to 3.2 by the addition of phosphoric acid.

The elution with these two solutions begins with 100% solution A for 15 minutes, followed by a gradual change over a 15 minute interval to 1:1 solution A:solution B. This ratio is held for 5 minutes. The ratio is then changed over a 15 minute interval to 100% solution B, and the elution is carried on for 5 more minutes with pure solution B.

EXAMPLE 1

Preparation of First Stage Inoculum

The following medium was prepared for use in the agar slant culture of *Nocardia orientalis* NRRL 15232:

| Ingredient | Amount (g/L) |
| --- | --- |
| Precooked oatmeal | 60.0 |
| Yeast | 2.5 |
| $K_2HPO_4$ | 1.0 |
| Czapek's mineral stock | 5.0 ml/L |
| Agar | 25.0 |
| Deionized water q.s. to | 1.0 liter |

Czapek's mineral stock is prepared from the following ingredients:

| Ingredient | Amount (g/100 ml) |
| --- | --- |
| KCl | 10.0 |
| $MgSO_4.7H_2O$ | 10.0 |
| $FeSO_4.7H_2O$ | 0.2 |
| Deionized water q.s. to | 100 ml. |

Pre-sterilization pH=6.2 Adjusted to pH 7.3 with aqueous sodium hydroxide solution. Post-sterilization pH=6.7.

Spores of *Nocardia orientalis* NRRL 15232 were inoculated on an agar slant made up of the above-identified ingredients, and the thus-inoculated slant was incubated for seven days at about 30° C. The mature slant culture was then covered with sterile distilled water and scraped with a sterile tool to loosen the spores and the mycelium. One milliliter of the resulting spore suspension was used to inoculate 50 ml of vegetative medium having the following composition:

| Ingredient | Amount (g/L) |
| --- | --- |
| Potato dextrin | 30.0 |
| Molasses, blackstrap | 20.0 |
| Bacto-peptone (Difco Laboratories) | 7.0 |
| L-Tyrosine | 1.0 |
| Deionized water q.s. to | 1.0 liter |

The mixture had pH=5.5, which was adjusted to pH 7.0 with aqueous sodium hydroxide solution before sterilization. Post-sterilization pH=6.1.

The vegetative inoculum was incubated in a 250-ml wide-mouth Erlenmeyer flask at about 30° C. for about 48 hours on a shaker rotating through an arc two inches in diameter at 250 RPM. This incubated medium is used either to inoculate small fermenters (the inoculum being 0.8% per volume of medium) or to inoculate second stage flasks for the production of a larger volume of mycelium.

Fermentation of A-51568.1

One hundred liters of a production medium was inoculated with 0.8% (800 ml) of the incubated vegetative medium from above. The production medium had the following composition:

| Ingredient | Amount (g/L) |
| --- | --- |
| Polypropyleneglycol (2000) | 0.2 |
| Potato dextrin | 30.0 |
| Blackstrap molasses | 20.0 |
| Bacto-peptone (Difco Laboratories) | 7.0 |
| L-Tyrosine | 1.0 |
| Deionized water q.s to | 100 liters |

The medium had pH 5.2, which was adjusted to 7.1 with aqueous 5N sodium hydroxide. The medium was sterilized at 121° C. at 17–19 psi. for 45 minutes. After sterilization, the medium had pH 6.2.

The inoculated production medium was allowed to ferment in a 165-liter fermentation tank for about 114 hours at a temperature of 30° C. The fermentation medium was aerated with sterile air at a rate of 0.125 v/v/m, and was stirred with conventional agitators at about 200 RPM.

The antibiotic activity is present in the supernatant of the fermentation mixture. The presence of the antibiotic activity was checked by centrifuging a sample of the whole broth at 1000×g, and decanting the centrate for assay. The sample is diluted with pH 6.0 phosphate buffer, and assayed microbiologically in an agar-well plate test using as assay organism *Micrococcus luteus* ATCC 9341.

The fermentation was also monitored qualitatively by a thin-layer chromatography (TLC) system using silica gel #5763 or #5765 plates from E. Merck, Darmstadt. The plates were developed in a solvent system containing chloroform:methanol:ammonia:n-butanol:water (25:50:25:10). The chromatograms were bioautographed versus *Bacillus subtilis* ATCC 6633 on nutrient agar plates.

Employing the chloroform:methanol:ammonia:n-butanol:water (25:50:25:10) solvent, the antibiotic A-51568 has been determined to have an $R_f$ value of 0.6.

EXAMPLE 2

Isolation of Antibiotic A-51568 and A-51568B Mixture

To three liters of the above whole fermentation broth there was added filter aid (Hyflo Supercel, a diatomaceous earth, Johns-Manville Corp.), and the mixture filtered. The filtrate, which measured 2.7 liters and had pH=7.8, was applied to Diaion HP-20 resin (a highly porous, styrenedivinylbenzene copolymer in bead form, Mitsubishi Chemical Industries, Ltd., Tokyo, Japan) contained in a 3×25 cm chromatography column. The effluent was discarded, and the column washed with 1 liter of water and 500 ml of 25 percent methanol in water. The antibiotic A-51568 and A-51568B mixture was eluted from the column with two 500-ml portions of 50 percent methanol in water. The eluant was assayed for antibiotic activity using *B. subtilis*. The more active fraction was concentrated to a small volume and lyophilized. An A-51568 and A-51568B mixture weighing 905 mg was obtained.

EXAMPLE 3

Purification of Antibiotic A-51568

The A-51568 and A-51568B antibiotic mixture (905 mg, from Example 2, above) was dissolved in 50 ml of water and applied to Sephadex CM-25 ($NH_4^+$ cycle) (Pharmacia Fine Chemicals AB, Uppsala, Sweden) contained in a 1.7×44 cm chromatography column. The effluent was discarded and the column washed with 250 ml of water. The column was then eluted with a convex gradient of ammonium bicarbonate (H$_2$O→1M NH$_4$HCO$_3$; 100 ml mixing chamber). Fifty 25-ml fractions were collected and checked for antibiotic activity using a *B. subtilis* assay.

Active fractions, that is, those containing antibiotic activity, were pooled and applied to a 1.7×10 cm chromatography column of Diaion HP-20 resin previously equilibrated in water. After the application of the antibiotic solution, the column was washed with 200 ml of water and eluted with 100 ml of 50 percent methanol in water. The methanol eluate was evaporated to dryness, the residue dissolved in a small amount of water and acidified with 0.1N aqueous hydrochloric acid. The acidified mixture was then lyophilized. There was obtained 25 mg of pure antibiotic A-51568.

EXAMPLE 4

Preparation of First Stage Inoculum

The following medium was prepared for use in the agar slant culture of *Nocardia orientalis* NRRL 15232:

| Ingredient | Amount (g/L) |
| --- | --- |
| Precooked oatmeal | 60.0 |
| Yeast | 2.5 |
| K$_2$HPO | 1.0 |
| Czapek's mineral stock | 5.0 ml/L |
| Agar | 25.0 |
| Deionized water q.s. to | 1.0 liter |

Czapek's mineral stock was prepared from the following ingredients:

| Ingredient | Amount (g/100 ml) | |
| --- | --- | --- |
| KCl | 10.0 | |
| MgSO$_4$.7H$_2$O | 10.0 | |
| FeSO$_4$. 7H$_2$O | 0.2 | |
| Deionized water q.s. to | 100 | ml. |

Pre-sterilization pH=6.2 Adjusted to pH 7.3 with aqueous sodium hydroxide solution. Post-sterilization pH=6.7.

Spores of *Nocardia orientalis* NRRL 15232 were inoculated on an agar slant made up of the above-identified ingredients, and the inoculated slant was incubated for seven days at 30° C. The mature slant culture was then covered with sterile distilled water and scraped with a sterile tool to loosen the spores and the mycelia. One milliliter of the resulting spore suspension was used to inoculate 50 ml of vegetative medium having the following composition:

| Ingredient | Amount (g/L) |
| --- | --- |
| Glucose | 15.0 |
| Potato Dextrin | 20.0 |
| Soybean grits | 15.0 |
| Corn Steep Liquor | 10.0 |
| Yeast Extract | 1.0 |
| CaCO$_3$ | 2.0 |
| Tap Water q.s. to | 1.0 liter |

The medium had a pH of 5.5, which was adjusted to pH 6.5 with 5N sodium hydroxide solution before sterilization. Post-sterilization pH was 6.6.

The vegetative inoculum was incubated in a 250-ml wide-mouth Erlenmeyer flask at 30° C. for about 46 hours on a shaker rotating through an arc two inches in diameter at 250 RPM. This incubated medium was used to inoculate second stage flasks for the production of a larger volume of mycelia.

Specifically, one 10 ml portion per flask of the above 250 ml flask inoculum was used to inoculate two 400 ml portions of a medium with the identical composition to the above vegetative medium. These two 400 ml portions were each incubated in 2000 ml widemouth Erlenmeyer flasks at 30° C. for about 51 hours on a shaker rotating through an arc two inches in diameter at 250 RPM.

Fermentation of A-51568.1

One hundred ten liters of a production medium was inoculated with approximately 0.8% (800 ml) obtained from combined volumes of the two second-stage incubated vegetative media from above. The production medium had the following composition:

| Ingredient | Amount (g/L) |
| --- | --- |
| SAG 471 (UNION CARBIDE) | 0.2 |
| Polypropyleneglycol (2000) | 0.1 |
| Potato dextrin | 30.0 |
| Blackstrap molasses | 20.0 |
| Bacto-peptone (Difco Labs.) | 7.0 |
| L-Tyrosine | 1.0 |
| Deionized water q.s. to | 110 liters |

The pH of the medium was 5.5, and was adjusted to 7.0 with aqueous 5N sodium hydroxide. The medium was sterilized at 121° C. at 17-19 psi. for 45 minutes. After sterilization, the pH of the medium was 6.2.

The inoculated production medium was fermented in a 165-liter fermentation tank for about 114 hours at a temperature of 30° C. The fermentation medium was aerated with sterile air at a rate of 0.125 v/v/m, and was stirred with conventional agitators at about 250 RPM.

The antibiotic activity is present in the supernatant of the fermentation mixture. The presence of the antibiotic activity was checked by centrifuging a sample of the whole broth at 1000×g, and decanting the centrate for assay. The sample was diluted with pH 6.0 phosphate buffer, and assayed microbiologically in an agar-well plate test using as an assay organism *Micrococcus luteus* ATCC 9341. Two fermentations using the above conditions were carried out.

EXAMPLE 5

Isolation of Antibiotic A-51568 and A-51568B Mixture

The whole broths of the above two one-hundred-ten-liter-scale fermentations were combined (approximately 230 L, total), Hyflo-Supercel (diatomaceous earth filter aid) was added and the broth was filtered using a 36" Plate Frame Filter (Sperry). The pH of the filtrate (185 L) was adjusted 6.0-6.5 by the addition of 5N hydrochloric acid. The A-51568 factors were adsorbed onto Ionac X-236 Resin (H+) (4 L. of resin per 100 L. of filtrate) and the mixture was stirred to allow adsorption of the activity. The supernatant was discarded and the resin was washed with water (10 resin volumes, approximately 40 L.). After discarding the wash, the X-236 resin was loaded into a column which was eluted with 0.1N ammonium hydroxide (5 column volumes). Antibiotic activity of the 4-liter fractions was monitored by disc plate, bioassay and HPLC. The pH of the fractions containing the two A-51568 factors was adjusted to 7.0 by the addition of 5N hydrochloric acid then pooled and loaded onto a column of Diaion HP-20 resin (5 L. of resin, 4" I.D.×42" L.) to desalt the mixture. The loading ratio of the active fractions was equivalent to 20 g vancomycin activity/liter of resin. The amount of activity present was determined by bioassay as described above. The effluent was discarded. The resin was then eluted with an aqueous solution of 5% isopropyl alcohol and 0.1% $H_3PO_4$. Fractions of 500 ml were collected and monitored for antibiotic activity using bioassay and HPLC analysis. Active fractions were combined, concentrated, and lyophilized. The resulting impure material contained about 95% A-51568 and 5% of A-51568B.

EXAMPLE 6

Purification of Antibiotics A-51568 and A-51568B

To further purify the product and to simultaneously aid the separation of A-51568 and A-51568B, the lyophile from Example 5 (14.7 g) was reconstituted with deionized water (200 ml) then loaded onto CM Sephadex C-25 ($NH_4^\oplus$ cycle, 5 l of resin) (Pharmacia Fine Chemicals AB, Uppsala, Sweden) contained on a 4" I.D.×42" length glass column. The column was eluted with a linear gradient of water to 0.25N aqueous ammonium bicarbonate. The 1-liter fractions that were collected were then neutralized by the addition of 5N hydrochloric acid and the antibiotic activity of the fractions monitored by disc plate and bioassay. Also an aliquot of each of the fractions was analyzed by HPLC. A-51568 and/or A-51568B-containing fractions were grouped into 2 pools based on the ratio of A-51568 to A-51568B contained in each fraction. Pool 1 consisted of fractions 10 and 11 which contained roughly a 1:1 ratio of A-51568 to A-51568B. Pool 2 consisted of fractions 12, 13, 14, 15 and 16 which contained predominantly A-51568. As in Example 5, the pools were desalted on HP-20 resin, using the same loading ratio based on the bioassay. Specifically, Pool 1 was loaded onto 50 ml of HP-20 resin contained in a ¼" I.D. column. Pool 2 was loaded on 500 ml of HP-20 resin contained in a 1.5" I.D.×2 ft column.

Both HP-20 columns were eluted with an aqueous solution of 5% isopropyl alcohol and 0.1% phosphoric acid. The 10 ml fractions collected from each of the columns were analyzed by bioassay and HPLC. The active fractions from each pool were lyophilized.

EXAMPLE 7

Separation of A-51568 and A-51568B

The lyophilized, desalted fractions from Pool 1 of Example 6 were chromatographed on the above-described HPLC system to give pure A-51568 and A-51568B.

We claim:

1. The method of producing antibiotic A-51568, which has the structure and its pharmaceutically-acceptable, non-toxic salts, which comprises (1) cultivating *Nocardia orientalis* NRRL 15232, or an A-51568-producing mutant or variant thereof, in a culture medium containing assimilable sources of carbon, nitrogen, and inorganic salts under submerged aerobic fermentation conditions until a substantial amount of antibiotic activity is produced, (2) isolating the mixture of A-51568 and A-51568B from the culture medium and (3) isolating A-51568 from the mixture of A-51568 and A-51568B.

2. A biologically pure culture of *Nocardia orientalis* NRRL 15232.

* * * * *